United States Patent
Iles et al.

(10) Patent No.: US 10,393,729 B2
(45) Date of Patent: Aug. 27, 2019

(54) PRENATAL SCREENING

(71) Applicant: Map IP Holding Limited, Cambridgeshire (GB)

(72) Inventors: Raymond Kruse Iles, Cambridgeshire (GB); Stephen Andrew Butler, Cambridgeshire (GB)

(73) Assignee: Map IP Holding Limited, Ely (GB)

( * ) Notice: Subject to any disclaimer, the term of this patent is extended or adjusted under 35 U.S.C. 154(b) by 0 days.

(21) Appl. No.: 14/779,058

(22) PCT Filed: Mar. 20, 2014

(86) PCT No.: PCT/GB2014/050876
§ 371 (c)(1),
(2) Date: Sep. 22, 2015

(87) PCT Pub. No.: WO2014/147404
PCT Pub. Date: Sep. 25, 2014

(65) Prior Publication Data
US 2016/0054293 A1    Feb. 25, 2016

(30) Foreign Application Priority Data
Mar. 22, 2013    (GB) .................................. 1305317.8

(51) Int. Cl.
| | | |
|---|---|---|
| *G01N 33/493* | (2006.01) | |
| *G01N 33/68* | (2006.01) | |
| *H01J 49/00* | (2006.01) | |
| *H01J 49/40* | (2006.01) | |
| *G16H 50/20* | (2018.01) | |

(52) U.S. Cl.
CPC ......... *G01N 33/493* (2013.01); *G01N 33/689* (2013.01); *G01N 33/6848* (2013.01); *G16H 50/20* (2018.01); *H01J 49/0027* (2013.01); *H01J 49/40* (2013.01)

(58) Field of Classification Search
USPC ....................................................... 250/282
See application file for complete search history.

(56) References Cited

U.S. PATENT DOCUMENTS

| | | | | |
|---|---|---|---|---|
| 7,191,068 | B2* | 3/2007 | Rosenfeld .......... | G01N 33/6803 702/19 |
| 7,425,700 | B2* | 9/2008 | Stults .................... | H01J 49/165 250/288 |
| 7,991,557 | B2* | 8/2011 | Liew ...................... | G16B 40/00 702/19 |
| 2010/0323911 | A1* | 12/2010 | Devarajan ............ | G01N 33/564 506/9 |
| 2015/0080263 | A1* | 3/2015 | Bahado-Singh ....... | G01N 33/50 506/12 |

FOREIGN PATENT DOCUMENTS

| WO | WO97003363 | 7/1996 |
|---|---|---|
| WO | WO03065043 | 8/2003 |

OTHER PUBLICATIONS

Gervais; et.al., "Glycosylation of human recombinant gonadotrophins: characterization and batch-to-batch consistency", Glycobiology vol. 13 No. 3, 2003 pp. 179-189.*
E.S. Jacoby et al., "Determination of the glycoforms of human chorionic gonadotropin beta-core fragment by matrix-assisted laser desorption/ionization time-of-flight mass spectrometry", Clinical Chemistry, 2000, 46(11):1796-1803.
S. Malatos et al., "Analysis of hCG beta core fragment glycosylation in normal and aberrant pregnancy by matrix-assisted laser desorption/ionisation time-of-flight mass spectrometry", 23rd Joint Meeting of the British Endocrine Societies With the European Federation of Endocrine Societies, 2004, 195.
M.M Elliott et al., "Carbohydrate and Peptide Structure of the α- and β-Subunits of Human Chorionic Gonadotropin From Normal and Aberrant Pregnancy and Choriocarcinoma", Endocrine, 1997, 7(1):15-32.

* cited by examiner

*Primary Examiner* — Phillip A Johnston
(74) *Attorney, Agent, or Firm* — Diederiks & Whitelaw, PLC.

(57) ABSTRACT

The present invention relates to a method for screening maternal urine samples for changes in the pattern of mass spectral fingerprinting which have been found to be characteristic of fetal aneuploidies such as Down's Syndrome and have application for the 5 screening of other fetal abnormalities and disorders of pregnancy including gestational trophoblastic diseases.

6 Claims, 2 Drawing Sheets

Down's Prediction Score=
(m/z 11300)+(m/z 11400)+(m/z 11500)+ (m/z 11600)+ (m/z 11700)+ (m/z 11800)+ (m/z 11900)

PRENATAL SCREENING

CROSS-REFERENCE TO RELATED APPLICATIONS

This application is a 35 U.S.C. § 371 national phase application of PCT Application No. PCT/GB2014/050876, filed Mar. 20, 2014, which claims priority to Great Britain Application No. 1305317.8 filed Mar. 22, 2013, each of which is incorporated herein by reference in its entirety.

FIELD OF THE INVENTION

The present invention relates to a method for screening maternal urine samples for changes in the pattern of mass spectral fingerprinting which have been found to be characteristic of fetal aneuploidies such as Down's Syndrome and have application for the screening of other fetal abnormalities and disorders of pregnancy including gestational trophoblastic diseases.

In particular, it relates to a method of detecting fetal aneuploidy such as Downs Syndrome, Patau syndrome Turner Syndrome, Klinefelter syndrome, Edwards syndrome and triple-X.

BACKGROUND TO THE INVENTION

Trisomy 21, commonly known as Downs Syndrome, is characterised by an extra copy of chromosome 21 and is one of the most common serious congenital abnormalities resulting in the most frequent single cause of significant learning disability in children of school age. People afflicted with Downs Syndrome have severe mental retardation, reduced life expectancy and abnormal immune response that predisposes them to serious infections. 40% of Downs Syndrome sufferers have congenital heart disease and an increased risk of developing leukaemia. All people over 40 with Down's Syndrome are liable to develop neuropathological changes characteristic of Alzheimer's disease.

The definitive test for Down's Syndrome in early pregnancy, i.e. at about 15 to 16 weeks, is karyotyping following amniocentesis. The sampling of amniotic fluid required for this carries the risk of inducing spontaneous miscarriage, which may occur in about 1 in 100 cases.

Originally maternal age was the only factor used to identify women at high risk of having a Downs Syndrome baby. At age 40 the chance of having a Downs baby is 1 in 100. This has led to many hospitals offering amniocentesis to women over a certain age, usually 35 or 37. However, this will only identify 15-30% of all cases of Down's syndrome as the majority still occur in women who are younger.

Over the past 25 years multiple marker blood tests have been developed to screen for Downs Syndrome. Serum alpha-fetoprotein (AFP) plus human chorionic gonadotrophin (hCG) are the most common markers. More recently, however, unconjugated estriol ($uE_3$) and inhibin A have been added to the markers screened for.

Screening performance varies according to the choice of markers used and whether ultrasound is used to estimate gestational age and to measure nuchal fold thickness at 15-22 weeks. When screening for serum markers and ultrasound are used in combination with maternal age, the detection rate for a 5% false-positive rate is estimated to be 59% for the double test (AFP+hCG), 69% for the triple test (AFP, hCG, $uE_3$) and 76% for the quadruple test which includes inhibin A.

Current screening technology is expensive and requires the minimal invasive procedure of blood sampling together with mathematical modelling of values detected corrected against level changes due to gestation age.

Human chorionic gonadotropin (hCG) is a glycopeptide hormone produced by the syncytiotrophoblasts of the fetal placenta, and has a molecular weight of about 38 kilodaltons. It can be detected by immunoassay in the maternal urine within days after fertilisation. The intact hCG molecule is a heterodimer comprising a specific β 25 subunit non-covalently bound to an α subunit, which is common to other glycoproteins.

Maternal serum levels of both intact hCG and the free β-subunit are elevated on average in Down's Syndrome, but the extent of elevation is greater for 30 free β-hCG. HCG is detected in both the serum and urine of pregnant women, as are the free α and β subunits of hCG, as well as the degradation products of hCG and of free β-subunit hCG.

The terminal degradation product of the β-subunit of hCG is urinary gonadotropin peptide (UGP), otherwise known as β-core-hCG, β-core fragment, β-core or urinary gonadotrophin fragment (uGF).

UGP is excreted into urine. WO97/03363 describes a pre-natal urinary screening method for Down's Syndrome which comprises testing a maternal urine sample during the first trimester of pregnancy to determine whether the level of UGP in the sample is elevated above the level of UGP found in urine samples from normal 10 pregnancies. The method described in WO 97/03363 utilises immunoassays specific for UGP.

The precise structure of hCG has been well characterised by HPLC-mass spectrometry and by crystallographic analysis. Using trypsin digestion, peptide mass mapping of hCG and its subunits has been carried out using matrix-assisted laser desorption/ionization time-of-flight mass spectrometry (MALDI-ToF MS). Jacoby, E. S. et al in Clinical Chemistry, 46 (11), 1796-1803 (2000) described the purification from pregnancy urine of hCGβ-Core fragment (hCGβcf), which was reduced by dithiothreitol (DTT) reduction and analysed by MALDI-ToF MS. They concluded that the mass spectrum of DTT-reduced hCGβcf that was produced, whilst not precisely defining hCG β cf glycosylation, would appear to result in a distinctive "fingerprint". MALDI-ToF MS analysis of unextracted urine samples from pregnant women showed only a broad peak corresponding to proteinated hCGβcf.

WO03/065043 describes the immobilisation of immunoglobins on a MALDI-TOF MS target which may then be used in the identification and relative quantification of proteins such as hCGβcf.

Human chorionic gonadotropin (hCG) is a hetro-dimeric glycoprotein hormone with 8 glycosylation sites containing four N-linked oligosaccharides and four O-linked oligosaccharides. The N-linked oligosaccharides are attached to the polypeptide chain by β-N-glycosidic bonds on asparagine residues; two are on the α and two are on the β-subunit. They share the same basic structural characteristics: N-acetyl glucososamine (GLcNAc) is attached to an asparagine residue followed by another GLcNAc, mannose and two more branches of mannose. This is the monantennary pentasaccharide core with the remaining components being variable. The O-linked oligosaccharides are attached by α-β-glycosidic bonds onto serine residues of the β-subunit carboxyl terminal peptide.

Carbohydrate heterogeneity has been extensively reported for the free β-subunit of hCG (hCG β) with variable mono-, bi- and triantennary carbohydrate structures being found in normal and abnormal pregnancies (Elliott M M, Kardana A, Lustbader J W, Cole L A. Endocrine. 1997 August; 7(1):15-32. Carbohydrate and peptide structure of the alpha- and beta-subunits of human chorionic gonadotropin from normal and aberrant pregnancy and choriocarcinoma).

The degradation product of the β-subunit of hCG known as β-core fragment (hCG β cf) is composed of peptides from the β-subunit of hCG, i.e peptides β 6-40 and β 55-92, connected by four disulfide bridges. It retains many of the antigenic determinates of the original hCG β molecule prior to metabolism, which occurs primarily in the kidney. The β 6-40 polypeptide chain contains the two hCG β N-linked carbohydrate moieties, although the oligosaccharides are truncated due to metabolism.

Whilst hCG β cf glycosylation has been studied using MALDI-ToF MS, which resulted in a mass spectrum that appeared to give a distinctive "finger print", the method used involved a pre-treatment of samples with dithiothreitol to reduce the mass of peptides thus bringing them into a relatively optimum resolution range of the mass spectrometer. MALDI-ToF MS analysis, according to Jacoby et al (2000) resulted in a broad peak corresponding to protonated hCG β cf.

The disadvantage of MALDI-ToF MS is that it is not a quantitative technique. Consequently, the raw mass spectra produced cannot be used directly to produce comparative data for diagnostic test algorithms.

STATEMENTS OF THE INVENTION hCG glycosylation is extremely variable and hyperglycosylation of hCG occurs in disorders of pregnancy and fetal aneuploidies such as Down's Syndrome. It has now been found that, by subjecting unextracted, untreated urine samples obtained from pregnant women up to the second trimester, preferably between the 7th and 13th week of gestation, to MADLI-ToF MS analysis, a unique mass spectra is obtained which may show the change in pattern in glycosylation variants. These changes in pattern are indicative of the metabolic products of hyperglycosylated hCG that are characteristic of the glycosylation processes in cells of the trophoblast in disorders of pregnancy and fetal aneuploidy, and thus indicative of these conditions.

According to one aspect of the present invention, there is provided a method of detecting a disorder of pregnancy or fetal aneuploidy up to the second trimester comprising, subjecting a maternal urine sample from a pregnant woman to direct mass spectral analysis, and comparing the patterns resulting from said analysis to mass spectral patterns obtained from normal pregnancies to determine whether said patterns from said sample are indicative of a disorder of pregnancy or fetal aneuploidy According to one aspect of the present invention, there is provided a method of detecting fetal aneuploidy up to the second trimester comprising subjecting a maternal urine sample from a pregnant woman to direct mass spectral analysis, and comparing the patterns resulting from said analysis to mass spectral patterns obtained from non-aneuploid pregnancies to determine whether said patterns from said sample are indicative of fetal aneuploidy The method of the invention provides a means of screening subjects to identify those mothers who are at risk of having or developing a disorder of pregnancy, or carrying an aneuploidy fetus.

As used herein a disorder of pregnancy includes Ectopic pregnancy, Threatened Miscarriage, Hyperemesis Gravidarum and Gestational Trophoblastic Diseases, Placental Insufficiency, Pre-eclampsia, Gestational Diabetes, Obstetric Cholestasis, and Recurrent Miscarriage in both normal and assisted reproduction. The method of the invention provides a method of screening for pregnancy disorders which are already present when the sample is obtained such as Ectopic pregnancy, Threatened Miscarriage, Hyperemesis Gravidarum and Gestational Trophoblastic Diseases. The method of the invention can also provide an indication of the risk of developing other disorders of pregnancy which generally occur later in the pregnancy (i.e. after the sample has been taken) such as Placental Insufficiency, Preeclampsia, Gestational Diabetes, Obstetric Cholestasis, and Recurrent Miscarriage in both normal and assisted reproduction. Thus the method has both diagnostic and prognostic value.

As used herein "fetal aneuploidy" refers to a condition wherein the fetus has more or less than 46 chromosomes. This results in conditions such as Downs Syndrome (Trisomy 21), Patau syndrome (Trisomy 13), Turner Syndrome (where all or part of one X chromosome is missing), Klinefelter syndrome (caused by an extra X chromosome in males), Edwards syndrome (Trisomy 18) and triple-X (caused by an extra X chromosome in females). Preferably the fetal aneuploidy is a trisomy disorder (e.g. Downs Syndrome, Patau syndrome and Edwards syndrome), more preferably Downs Syndrome.

"Direct mass spectral analysis" means that the data generated from the mass spectral analysis is used in the method, and not the inferred mass of the components present in the sample.

The method of the invention is carried out on a sample obtained up to, and including the second trimester of pregnancy. Preferably, the maternal urine sample is from a pregnant woman at between 7 and 16 weeks gestation, for example 7, 8, 9, 10, 11, 12, 13, 14, 15 or 16 weeks gestation. More preferably the maternal urine sample is from a pregnant woman at between 8 and 13 weeks gestation.

Preferably, the urine sample is a neat urine sample. Alternatively, the urine sample may be diluted or processed (concentrated, filtered, etc).

Preferably the urine sample is diluted. The urine sample may be diluted 1/100 (i.e. one part sample in 100 parts diluent), 1/500, 1/1000, 1/2500 or more. Most preferably the sample is diluted 1/1000 i.e one part urine sample in 1000 parts diluent. Preferably the diluent is water, more preferably deionized water.

Preferably the urine sample is not processed prior to dilution. Such processing includes concentrating the proteins of interest e.g. hCG; isolating hCG by for example HPLC or treatment with a chemical agent to disrupt or break intramolecular bonds. In particular, the sample is preferably not treated with a reducing agent. More preferably the sample is not treated with dithiothrietol (DTT).

Preferably, the patterns of mass spectra are determined by an automated quantitative method that can distinguish between a mass spectrum of a urine sample from a normal pregnant woman and the mass spectral pattern of a urine sample from a pregnant woman with a pregnancy disorder or an aneuploidy fetus. As used herein a "normal" pregnant woman is one who does not have a pregnancy disorder and has a non-aneuploid fetus.

As used herein an "automated quantitative method" refers to the processing by a computer software program of the direct output data from a mass spectrometer to which the sample was subjected.

Preferably, the patterns of mass spectra are determined by an automated quantitative method that can distinguish between a mass spectrum of a urine sample from a pregnant woman with a non-aneuploid fetus and the mass spectral pattern of a urine sample from a pregnant woman with an aneuploidy fetus. Methods of generating mass spectra, such as MALDI-Tof MS, are commonly not quantitative technique. For example the Y axis in these spectra is an indicator of "relative strength" of mass peak within the spectra, but not between mass peak in one sample versus another sample. In order to overcome this, normalisation needs to render Y axis value comparable between sample spectra. Normalization is the process of producing a data structure to reduce repetition and inconsistencies of data. Several normalisation techniques are possible. Typical normalisation methods include percentage of total area at a given point, Square difference and ratio of differences. The percentage difference is calculated as Percentage difference=(Yref−Y1/Yref×100%)

wherein Y ref is the minimum Y value of the spectra, and Y1 is Y value for each point.

The square difference is calculated as

Square Difference=(Y1−Yref)$^2$

The ratio difference is calculated as

Ratio Difference=(Ratio1−Ratio2).

Thus the data from the mass spectra is manipulated in order to provide a quantitative measure of the qualitative change shown on the spectra.

Preferably, each sample is compared against a reference spectral model. The "reference spectral model" is the expected mass within a set range, determined from statistical analysis of a collection of normal pregnancy urine samples at matched gestational age. Preferably the range is between about 500-100,000 m/z, for example 1,000-75,000 m/z, 2,500-50,000 m/z, 5,000-25,000 m/z or 6,000-14,000 m/z. Most preferably the range is 6,000-14,000 m/z. Preferably the spectral model of expected mass between about 6,000-14,000 m/z is determined from statistical analysis of a collection of non-aneuploidy pregnancy urine samples at matched gestational age.

Preferably, the spectral model is created by a method of data processing which results in a normalised statistically determined index of relative proportion of mass spectra within a set range. This renders all spectra comparable such that the median and centile variability at any given mass value can be modelled. Preferably the range is between about 6,000-14,000 m/z.

Preferably, a parallel "disease" model, as generated above from normalised statistically determined index of relative proportion of mass spectra within a set range is created from maternal urine obtained from a pregnant woman at between 8 and 16 weeks gestation with a disorder of pregnancy, or a fetal aneuploidy, for example Downs syndrome. Preferably the range is between about 6,000-14,000 m/z.

A normalised statistically determined index of relative proportion of mass spectra within a given range can be calculated from using the total area under the curve of mass spectra. This can then be used to calculate the relative intensity.

The area under the curve of mass spectra is calculated by dividing the mass spectra into a plurality of bins of a given number of m/z. As used herein "Bin" has its usual statistical meaning, for example, of being one of a series of ranges of numerical value into which data are sorted in statistical analysis. For example the bins can be 100 m/z, 50 m/z, 25 m/z, 10 m/z or 5 m/z in size. The smaller the size of the bin used, the more refined the method.

The relative intensity (Y Axis value) can be calculated by the "square of difference" method and therefore a comparable Y value given for every bin. In this method, the minimum Y value of the spectra (Y ref) was subtracted from the Y value at every bin and the difference was squared. The formula used to calculate square of difference=(y1−yref)$^2$ and the calculated square of difference was then named as "relative intensity".

After applying the normalization techniques, the ratio of normalized spectral value of samples obtained from women with normal pregnancy and those from women suffering from a pregnancy disorder or with an aneuploidy fetus (mean, standard deviation, skewness, upper and lower quartile, median, kurtosis as well as 95th and 5th centile) at 7 to 16 weeks gestation can be calculated.

The difference in relative intensity at each mass bin between samples obtained from women with normal pregnancy and those from women suffering from a pregnancy disorder or with an aneuploidy fetus at the respective gestational ages can be captured using commercially available statistical tests such as MATLAB Stats® Direct™ and Origin 8™.

The reference spectral model and the disease model, are then compared by plotting (for example as shown in FIG. 1) in order to identify 'hot spots' i.e. points of difference between the two models. This may be a decrease or increase in the size of a peak, or the appearance of a peak. The points of difference can then be used to determine the presence of an aneuploidy fetus, or likelihood of a pregnancy disorder. This may be done by using a suitable algorithm.

The specific regions from 6,000 to <8,000 m/z, from 9,000 to <9,600 m/z and from 10,900 to 12,000 m/z were identified as areas of mass spectral differences between samples from fetal aneuploid pregnancy and non aneuploid pregnancy. These areas of difference were used to create a Predictive Algorithm score=(m/z 11400)+(m/z 9200)/(m/z 6700) in particular for samples obtained at up to 14 weeks gestation, preferably samples taken at 12, 13 or 14 weeks gestation.

The specific regions from 10,900 to 12,000 m/z were identified as areas of mass spectral differences between samples from fetal aneuploid pregnancy and non aneuploid pregnancy in the second trimester. These areas of difference were used to create a Predictive Algorithm score=(m/z 11300)+(m/z 11400)+(m/z 11500)+(m/z 11600)+(m/z 11700)+(m/z 11800)+(m/z 11900) for samples obtained in the second trimester, preferably samples taken at 15, 16 or 17 weeks gestation The analysis of the mass spectra can be easily calculated using a suitable computer software program. A computer can also be programmed with the suitable algorithm in order to provide an indication of the presence of an aneuploidy fetus, or likelihood of a pregnancy disorder.

Preferably, the mass spectral analysis carried out is matrix-assisted laser desorption/ionization time-of-flight mass spectrometry (MALDI-ToF MS).

Also described is a method of detecting a disorder of pregnancy or fetal aneuploidy up to the second trimester comprising
a) obtaining a maternal urine sample form a pregnant woman;
b) subjecting the sample to direct mass spectral analysis;
c) comparing the patterns resulting from said analysis to mass spectral patterns obtained from a maternal urine sample from a normal pregnant woman to determine whether said patterns from said sample from a pregnant woman are indicative of a disorder of pregnancy or fetal aneuploidy.

Preferably the method detects fetal aneuploidy, and the patterns resulting from the analysis are compared to those from a woman with a non-aneuploidy pregnancy.

In this specification, the verb "comprise" has its normal dictionary meaning, to denote non-exclusive inclusion. That is, use of the word "comprise" (or any of its derivatives) to include one feature or more, does not exclude the possibility of also including further features. The word "preferable" (or any of its derivates) indicates one feature or more that is preferred but not essential.

All or any of the features disclosed in this specification (including any accompanying claims, abstract and drawings), and/or all or any of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The application will now be described in the examples below which refer to the following figures.

EXAMPLE 1

Figure 1:
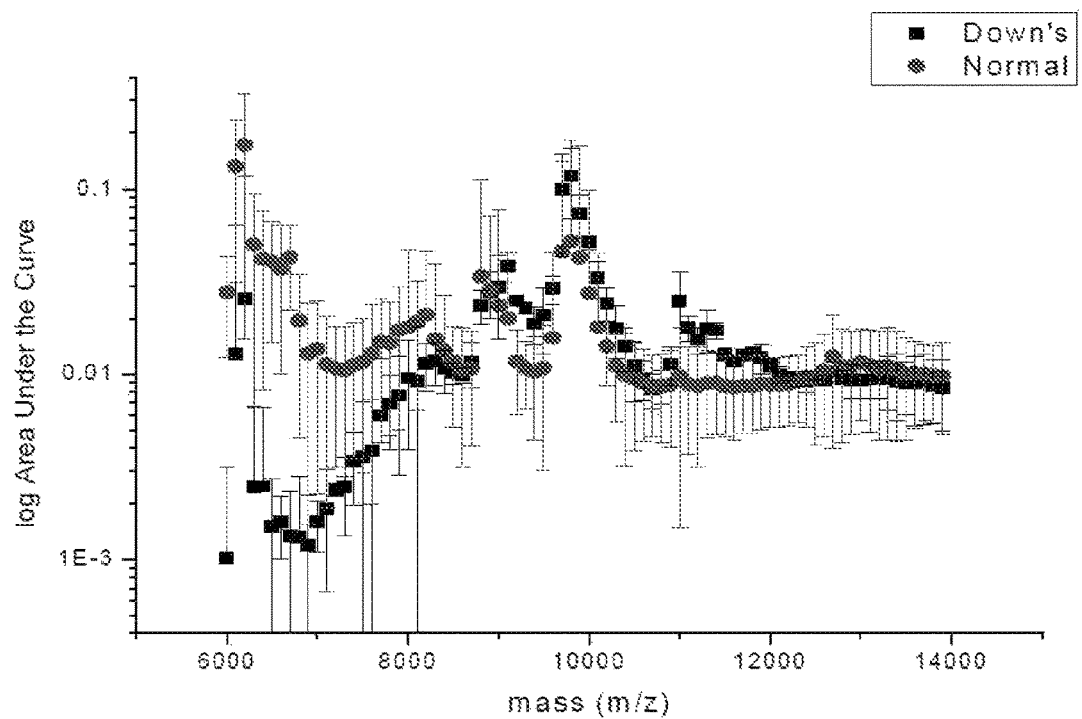
FIG. 1 shows a comparison based on a least squared normalization technique for Downs and non-aneuploid pregnancies at 12-14 weeks gestation.

An archival collection of 32 non-selected singleton pregnancy urine samples, disregarding maternal age and ethnicity, was used.

Prior to spotting onto the MALDI target plate for mass spectral analysis, the urine samples were spun down for 3 minutes at 1500 rpm to remove cellular debris. The samples were diluted in deionized water to between 1/100 to 1/1000 (parts sample/water)

MALDI plates (394 wells) were prepared by pipetting 0.5 µl of sinnapinic acid matrix solution (20 mg/ml dissolved in 50/50 v/v acetonitrile (ACN) and 0.1% trifluoroacetic acid (TFA) in ddH2O) and allowed to dry. A sample of diluted urine (0.5 µl) was added and then allowed to dry, followed by the addition of a further 0.5 µl of sinnapinic acid matrix solution. This was allowed to dry at room temperature for 1 hour before mass spectrometric analysis was performed.

The mass spectrometric analysis was carried out using a Shimadzu Axima plus MALDI mass spectrometer; the pulse nitrogen laser ($\lambda$max=337 nm), was fired at 90% power to desorb ions from each sample. The ions were accelerated by a 20 kV electrical field down a 1.2 m linear tube and detected by a micro-channel plate detector at a sampling rate of 500 MHz. Spectra were generated by summing 20-30 laser shots. A positive linear mode was used in order to acquire the spectra.

Mass calibration of the MALDI-ToF instrument was established by running samples of known precise masses. In order to calibrate the instrument for Downs Syndrome spectral fingerprinting horse heart cytochrome C at a concentration of 10 pmol/µl was run as the external calibrant. The two points calibration generated was at $[M+H]+=12.361$ Da and $[M+2H]2+=6181$ Da. In order to transfer spectral data as compatible data files between software programmes the spectra fingerprint between 6,000-14,000 m/z was then captured as a comma delimited (also known as CSV) numeric data sets.

Normalization:

Comma delimited data was then changed to M.file format in order to render it readable by MATLAB software.

The total area under the curve of each sample within the mass range of 6,000-14,000 m/z was calculated and the region was divided into 80 individual bins of 100 m/z unit.

The relative intensity (Y Axis value) was calculated by the "square of difference" method and therefore a comparable Y value was given for every bin. In this method, the minimum Y value of the spectra (Y ref) was subtracted from the Y value at every bin and the difference was squared. The formula used to calculate square of difference=$(y1-yref)^2$ and the calculated square of difference was then named as "relative intensity".

After applying each normalization technique, the ratio of normalized spectral value of uncomplicated pregnancies and aneuploid (mean, standard deviation, skewness, upper and lower quartile, median, kurtosis as well as 95th and 5th centile) at 12-13 gestation was calculated.

The difference in spectral intensity at each mass bin (every 100 m/z) between uncomplicated and aneuploid pregnancies at the respective gestational ages was captured using statistical tests, (Stats Direct™ & Origin 8™).

Results

Computational models for assessing the relative level of spectral intensity of a fingerprint pattern between 6,000 to 14,000 m/z in Down's syndrome compared to uncomplicated singleton pregnancies was produced by plotting the median 95th and the 5th centile of the log of normalized area under the curve of every bin versus mass to charge ratio (m/z) from 6,000 to 14,000 Dalton from pregnancy urine at gestational age 12-13.

FIG. 1 of the accompanying diagrammatic drawings shows a comparison based on a least squared normalization technique for Downs and non-aneuploid pregnancies at 12-14 weeks gestation. Panel A shows overlaid average mass spectra with bin median as solid shapes and 5 and 95th centiles as whiskers for Downs (squares) and non-aneuploid (circles) pregnancies at 6000 to 14,000 m/z.

Figure 2:
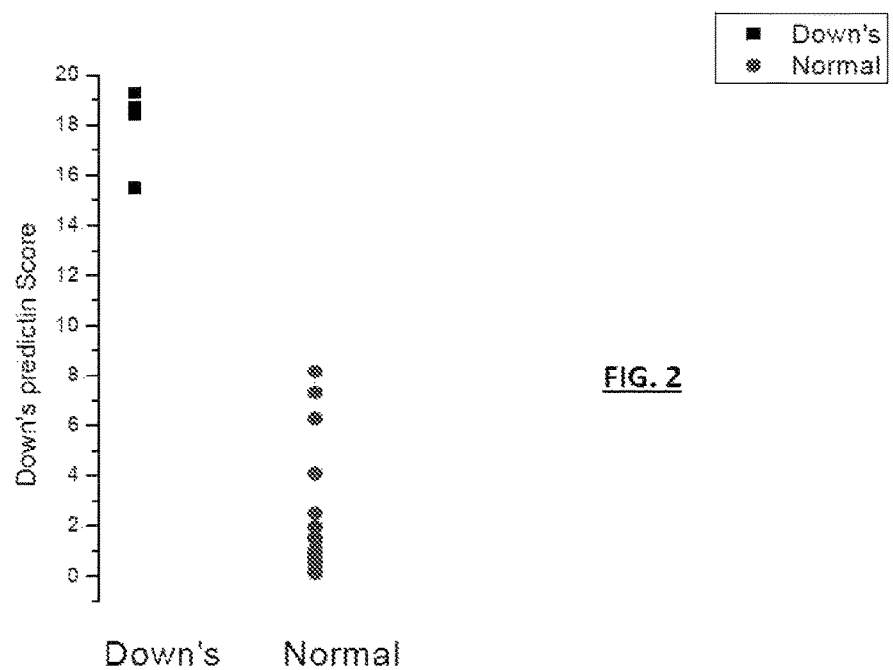
FIG. 2 is an illustration of a simple predictive algorithm for Downs Syndrome screening based on the spectral differences and comparison based on least squared normalization technique for Downs and non-aneuploid pregnancies at 12-14 weeks gestation.

FIG. 2 of the accompanying diagrammatic drawings is an illustration of a simple predictive algorithm for Downs Syndrome screening based on the spectral differences and comparison based on least squared normalization technique for Downs and non-aneuploid pregnancies at 12-14 weeks gestation as shown in FIG. 1. Three 'hot spots' were applied in a simple algorithm Predictive Algorithm score=(m/z 11400)+(m/z 9200)/(m/z 6700).

Total scores were calculated and plotted as a dot plot of the application of this algorithm on the six Downs syndrome and 33 non-aneuploid samples—thus, indicating a potential detection rate of >99.9% and false positive rates of <0.1% at a cut off of 9.

EXAMPLE 2

The methods of example 1 were repeated using samples of urine obtained during the second trimester, i.e. at 15, 16, and 17 weeks gestation.

Figure 3:
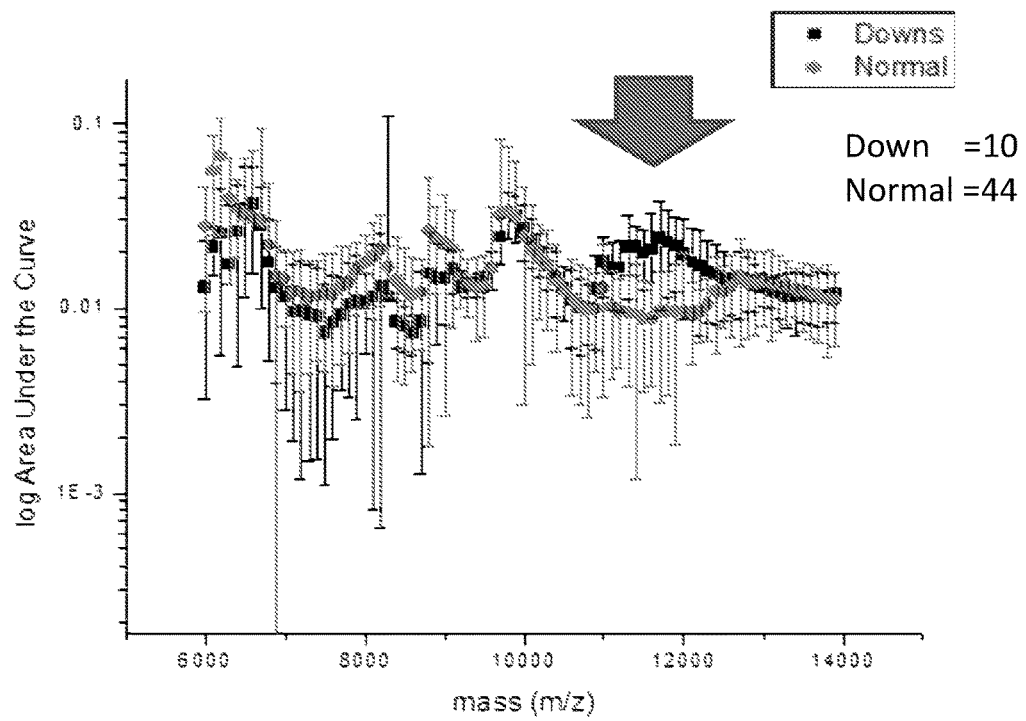
FIG. 3 shows a comparison based on a least squared normalization technique for Downs and non-aneuploid pregnancies at 15-17 weeks gestation.

FIG. 3 of the accompanying diagrammatic drawings shows a comparison based on a least squared normalization technique for Downs and non-aneuploid pregnancies at 15-17 weeks gestation. Panel A shows overlaid average mass spectra with bin median as solid shapes and 5 and 95th centiles as whiskers for Downs (squares) and non-aneuploid (circles) pregnancies at 6000 to 14,000 m/z.

Figure 4:
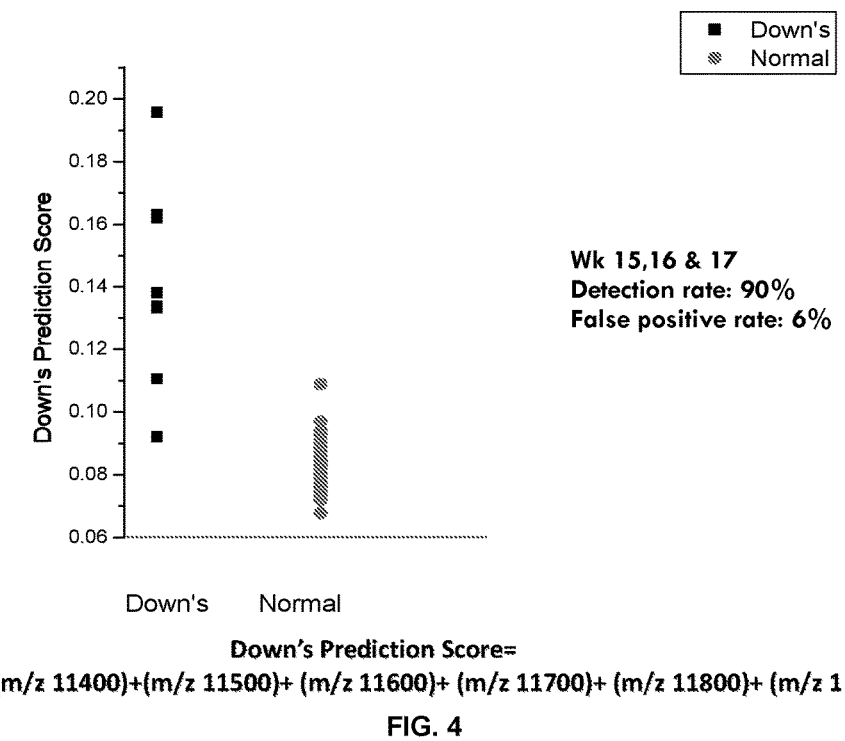
FIG. 4 is an illustration of a simple predictive algorithm for Downs Syndrome screening based on the spectral differences and comparison based on least squared normalization technique for Downs and non-aneuploid pregnancies at 15-17 weeks gestation as shown in FIG. 3. Seven 'hot spots' were applied in a simple algorithm.

FIG. 4 of the accompanying diagrammatic drawings is an illustration of a simple predictive algorithm for Downs Syndrome screening based on the spectral differences and comparison based on least squared normalization technique for Downs and non-aneuploid pregnancies at 15-17 weeks gestation as shown in FIG. 3. Seven 'hot spots' were applied in a simple algorithm.

Predictive Algorithm score=(m/z 11300)+(m/z 11400)+(m/z 11500)+(m/z 11600)+(m/z 11700)+(m/z 11800)+(m/z 11900)

Total scores were calculated and plotted as a dot plot of the application of this algorithm on the 10 Downs syndrome and 44 non-aneuploid samples—thus, indicating a potential detection rate of 90% and false positive rates of 6% at a cut off of 9.

EXAMPLE 3 ANALYSIS OF SAMPLES FOR DISORDERS OF PREGNANCY

Urine samples from women with gestational trophoblastic diseases (e.g. molar and hyperemesis gravidarum pregnancies) were compared to samples obtained from women with a normal pregnancy. hCGβcf hyperglycosylation due to tri-antennary glycoforms was found to be the highest in the urine from women with molar and hyperemesis gravidarum pregnancies compared to the samples from normal pregnancy. Although such molecules are subject to metabolic processing, this supports previously published data, which has shown that hCG is N-linked hyperglycosylated to a greater extent in disease and abnormal pregnancy. These differences in glycosylation of hCG, would result in a change of mass detectable by mass spectral analysis. These changes can be used in the methods of the invention in order to detect disorders of pregnancy, such as gestational trophoblastic diseases.

In this specification, the verb "comprise" has its normal dictionary meaning, to denote non-exclusive inclusion. That is, use of the word "comprise" (or any of its derivatives) to include one feature or more, does not exclude the possibility of also including further features. The word "preferable" (or any of its derivates) indicates one feature or more that is preferred but not essential.

All or any of the features disclosed in this specification (including any accompanying claims, abstract and drawings), and/or all or any of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method of detecting a fetal aneuploidy comprising:
subjecting a neat or dilute, unprocessed maternal urine sample obtained from a pregnant woman between 12-14 weeks gestation to direct mass spectral analysis, wherein the mass spectral analysis is matrix-assisted laser desorption/ionization time-of-flight mass spectrometry (MALDI-TOF MS); and
comparing normalised patterns resulting from said analysis to normalised mass spectral patterns in a range of 6,000-14,000 m/z obtained from normal pregnancies to determine whether said normalised patterns from said sample are indicative of a fetal aneuploidy,
wherein the normalised patterns of mass spectra are determined by an automated quantitative method that can distinguish between a normalised mass spectrum of a urine sample from a pregnant woman with a non-aneuploid fetus and the normalised mass spectral pattern of a urine sample from a pregnant woman with an aneuploidy fetus,
wherein the fetal aneuploidy is Downs syndrome, and
wherein the method further comprises:
calculating a Downs syndrome predictive score=(m/z 11400)+(m/z 9200)/(m/z 6700).

2. A method of detecting a fetal aneuploidy comprising:
subjecting a neat or dilute, unprocessed maternal urine sample obtained from a pregnant woman between 15-17 weeks gestation to direct mass spectral analysis, wherein the mass spectral analysis is matrix-assisted laser desorption/ionization time-of-flight mass spectrometry (MALDI-TOF MS); and
comparing the normalised patterns resulting from said analysis to normalised mass spectral patterns in a range of 6,000-14,000 m/z obtained from normal pregnancies to determine whether said normalised patterns from said sample are indicative of a fetal aneuploidy,
wherein normalised patterns of mass spectra are determined by an automated quantitative method that can distinguish between a normalised mass spectrum of a urine sample from a pregnant woman with a non-aneuploid fetus and the normalised mass spectral pattern of a urine sample from a pregnant woman with an aneuploidy fetus, wherein the fetal aneuploidy is Downs syndrome, and wherein the method further comprises:

calculating a Downs syndrome predictive score=(m/z 11300)+(m/z 11400)+(m/z 11500)+(m/z 11600)+(m/z 11700)+(m/z 11800)+(m/z 11900).

3. A method of detecting a fetal aneuploidy comprising:

subjecting a neat or dilute, unprocessed maternal urine sample obtained from a pregnant woman between 12-17 weeks gestation to direct mass spectral analysis, wherein the mass spectral analysis is matrix-assisted laser desorption/ionization time-of-flight mass spectrometry (MALDI-TOF MS); and comparing sample normalised patterns of mass spectral peaks resulting from said analysis to reference normalised patterns of mass spectral peaks in a range of 6,000-14,000 m/z obtained from normal pregnancies to determine whether said sample normalised patterns from said sample are indicative of a fetal aneuploidy, wherein the normalised patterns of mass spectral peaks are determined by an automated quantitative method that can distinguish between a normalised mass spectrum of a urine sample from a pregnant woman with a non-aneuploid fetus and a normalised mass spectrum of a urine sample from a pregnant woman with an aneuploidy fetus, wherein the fetal aneuploidy is Downs syndrome, and wherein the method further comprises:

calculating a Downs syndrome predictive score by summing values based on differences between the sample normalised patterns of mass spectral peaks and the reference normalised patterns of mass spectral peaks located at three or more mass to charge ratios.

4. The method of detecting a fetal aneuploidy according to claim 3, wherein calculating a Downs syndrome predictive score includes summing values based on differences in areas of peaks located at the three or more mass to charge ratios.

5. The method of detecting a fetal aneuploidy according to claim 4, further comprising concluding that Downs syndrome is present when the predictive score is above a preset value.

6. The method of detecting a fetal aneuploidy according to claim 3, wherein calculating a Downs syndrome predictive score includes summing values based on differences in a logarithm of areas of peaks located at the three or more mass to charge ratios.

* * * * *